United States Patent
Winkler et al.

(10) Patent No.: US 10,561,781 B2
(45) Date of Patent: Feb. 18, 2020

(54) BLOOD FILTERING DEVICE

(71) Applicant: Mann+Hummel GMBH, Ludwigsburg (DE)

(72) Inventors: Dagmar Winkler, Filderstadt (DE); Heike Rupp, Stuttgart (DE); Claudio Weiss, Illingen (DE); Karlheinz Muenkel, Oberderdingen-Flehingen (DE); Joachim Stinzendoerfer, Speyer (DE); Steffen Schuetz, Bietigheim-Bissingen (DE); Sascha Bauer, Auenwald (DE); Frank Bartel, Dingolfing (DE); Alfons-Alois Schwinghammer, Dingolfing (DE); Michael Fasold, Auenwald (DE); Dietmar Talmon-Gros, Oberstenfeld (DE); Norbert Strassenberger, Adlkofen (DE); Anton Rabanter, Marklkofen (DE)

(73) Assignee: MANN+HUMMEL GmbH, Ludwigsburg (DE)

( * ) Notice: Subject to any disclaimer, the term of this patent is extended or adjusted under 35 U.S.C. 154(b) by 830 days.

(21) Appl. No.: 14/967,302

(22) Filed: Dec. 12, 2015

(65) Prior Publication Data
US 2016/0106907 A1    Apr. 21, 2016

Related U.S. Application Data

(63) Continuation of application No. PCT/EP2014/071373, filed on Oct. 7, 2014.

(30) Foreign Application Priority Data

Oct. 15, 2013 (DE) .................. 10 2013 017 035

(51) Int. Cl.
*A61M 1/34* (2006.01)
*B01D 63/00* (2006.01)
(Continued)

(52) U.S. Cl.
CPC ......... *A61M 1/3496* (2013.01); *B01D 63/005* (2013.01); *B01D 63/02* (2013.01);
(Continued)

(58) Field of Classification Search
CPC ............ A61M 1/3635; A61M 2230/20; A61M 1/0281; A61M 1/34; A61M 1/3496;
(Continued)

(56) References Cited

U.S. PATENT DOCUMENTS 3,920,549 A * 11/1975 Gigliello ............. B01L 3/50215
                                                      210/516
4,744,955 A *  5/1988 Shapiro ................. B01L 3/0224
                                                      134/100.1
(Continued)

FOREIGN PATENT DOCUMENTS

DE        2100209 C       5/1972
DE        19507580 A1     8/1995

*Primary Examiner* — Lucas A Stelling
*Assistant Examiner* — Angel Olivera
(74) *Attorney, Agent, or Firm* — James Hasselbeck

(57) ABSTRACT

A blood filtering device has a filtration section with filter medium separating raw side and clean side. A first communication path connects raw side and a first variable blood reservoir volume; a second communication path connects raw side and a second variable blood reservoir volume coupled to a receptacle. When varying the first variable blood reservoir volume, blood contained therein flows through first communication path to raw side, plasma/serum passes through the filter medium from raw side to clean side, and residual blood flows from raw side through second communication path into the second variable blood reservoir (Continued)

volume. When varying the second variable blood reservoir volume, blood contained therein flows through second communication path to raw side, plasma/serum passes through the filter medium from raw side to clean side, and residual blood flows from raw side through first communication path into first variable blood reservoir volume.

10 Claims, 2 Drawing Sheets

(51) Int. Cl.
*B01D 63/02* (2006.01)
*B01D 61/28* (2006.01)
*B01D 61/14* (2006.01)
*B01D 61/24* (2006.01)
*B01D 61/18* (2006.01)
*A61M 1/36* (2006.01)
*A61B 5/15* (2006.01)

(52) U.S. Cl.
CPC ...... *A61B 5/150755* (2013.01); *A61M 1/3635* (2014.02); *A61M 1/3678* (2014.02); *A61M 2230/20* (2013.01); *B01D 61/14* (2013.01); *B01D 61/142* (2013.01); *B01D 61/147* (2013.01); *B01D 61/18* (2013.01); *B01D 61/24* (2013.01); *B01D 61/246* (2013.01); *B01D 61/28* (2013.01); *B01D 63/028* (2013.01); *B01D 63/029* (2013.01); *B01D 2311/14* (2013.01); *B01D 2315/08* (2013.01); *B01D 2315/14* (2013.01); *B01D 2319/04* (2013.01); *G01N 2201/0221* (2013.01); *G01N 2201/0222* (2013.01); *G01N 2800/22* (2013.01)

(58) Field of Classification Search
CPC .... A61M 1/36; A61M 1/3633; A61M 1/3678; A61M 2205/3331; G01N 33/491; G01N 1/4005; G01N 2001/4016; G01N 2201/0221; G01N 2201/0222; G01N 2800/22; B01D 61/14; B01D 61/18; B01D 61/24; B01D 61/28; B01D 61/142; B01D 61/147; B01D 61/246; B01D 63/005; B01D 63/02; B01D 63/021; B01D 63/028; B01D 63/029; B01D 65/00; B01D 67/0088; B01D 2311/02; B01D 2311/14; B01D 3212/10; B01D 3212/12; B01D 3212/20; B01D 3212/24; B01D 3212/90; B01D 2315/08; B01D 2315/14; B01D 2319/04; B01D 2121/04; A61B 5/15003; A61B 5/150755; A61B 5/150229; A61B 5/150236; A61B 5/150244; A61B 5/150251; A61B 5/150389; A61B 5/150503; A61B 5/153; B01L 3/502; B01L 2300/0681; B01L 2400/0478; B01L 2400/0481
See application file for complete search history.

(56) References Cited

U.S. PATENT DOCUMENTS

| 5,674,394 | A | 10/1997 | Whitmore |
| 5,935,437 | A * | 8/1999 | Whitmore ........... A61M 1/3496 206/438 |
| 6,936,473 | B2 | 8/2005 | Nanba |
| 7,354,515 | B2 | 4/2008 | Coull et al. |
| 2004/0035792 | A1 | 2/2004 | Rauch |
| 2005/0205498 | A1* | 9/2005 | Sowemimo-Coker ..................... A61K 35/15 210/782 |

* cited by examiner

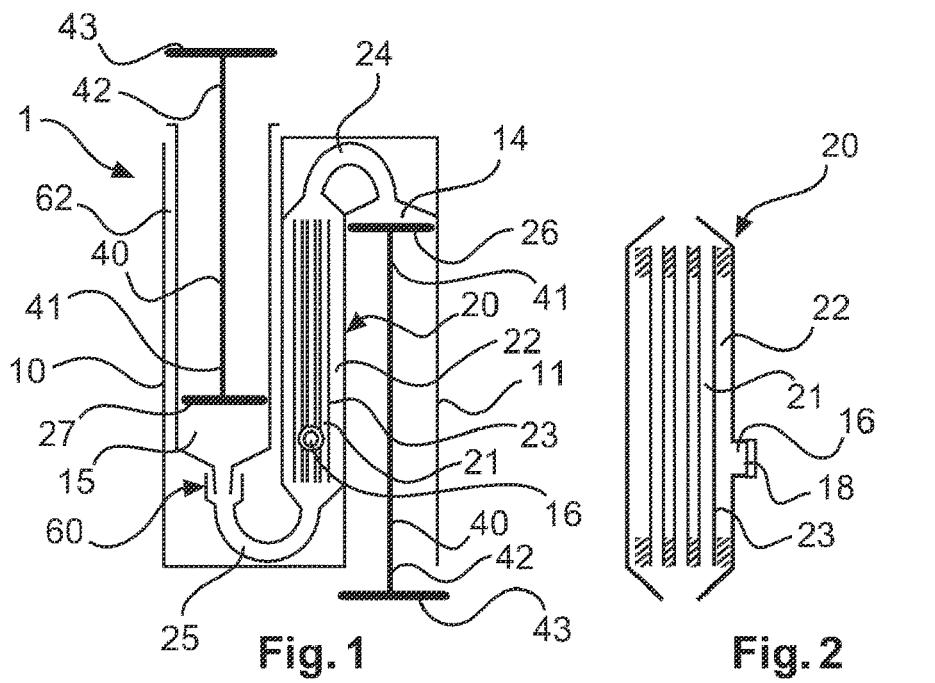
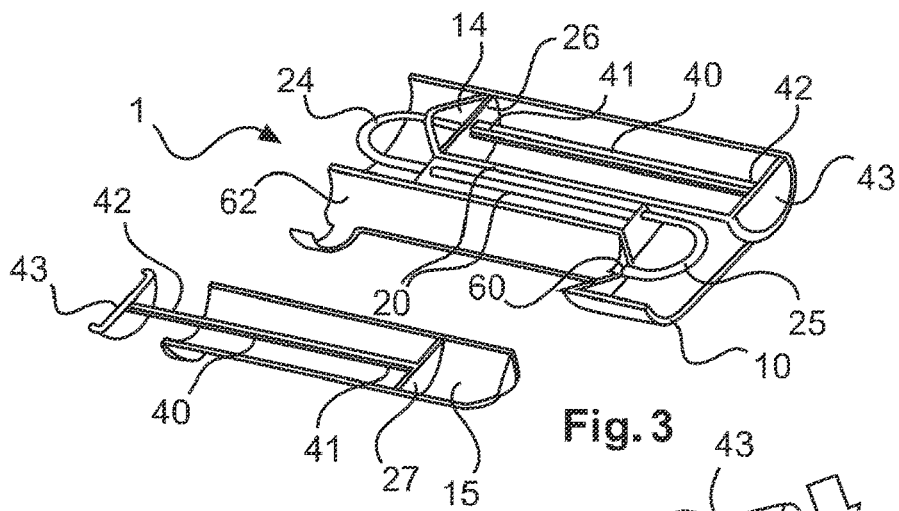
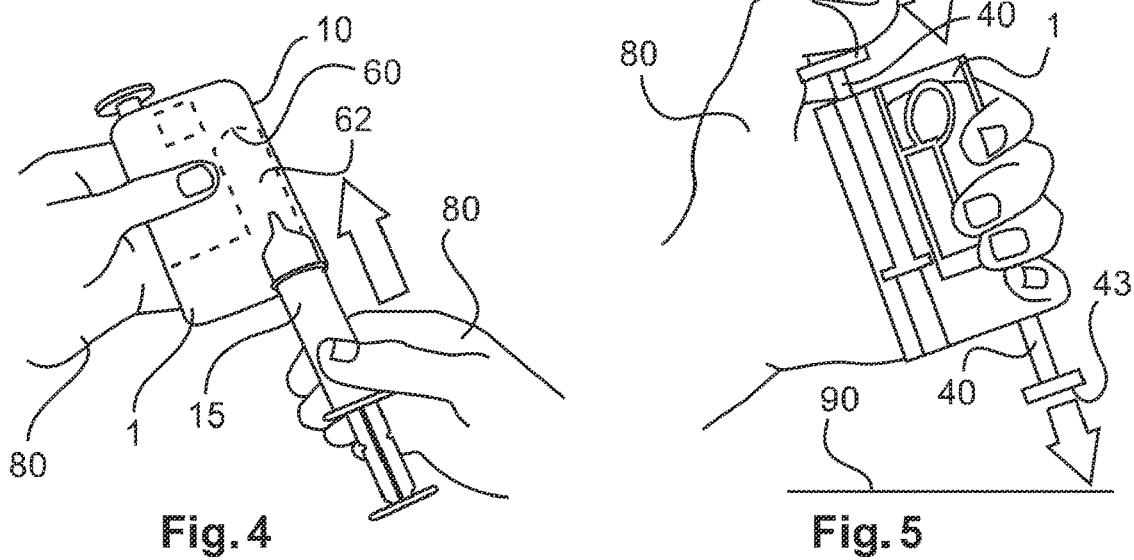

BLOOD FILTERING DEVICE

TECHNICAL FIELD

The present invention relates to a device for blood filtering, in particular to a blood filtering device allowing a quick and simple filtration process for the separation of blood cells.

Blood filtering is required for the separation of the specific components of the human blood. In particular, the separation is required as particular analysis may be carried out on particular components of the human blood only, wherein other blood components may disturb the analysis. The human blood has different components, for example, erythrocytes (red blood cells), which may have a size of about 7 μm to 8 μm, leucocytes (white blood cells), which may have a size of about 8 μm to 20 μm, and thrombocytes (platelets), which may have a size of about 1.5 μm to 3 μm, as well as the blood plasma. The erythrocytes, the leucocytes, and the thrombocytes represent more than 40 vol.-% of the whole blood. In order to separate the different components of the human blood, a centrifugation process has been established. However, a centrifugation process requires a considerable amount of time and an apparatus of considerable complexity. For particular purposes, it may be required to obtain a separation of the blood components in a short time and with an apparatus of minimum complexity. Further, it may be required to provide an apparatus which is easy to handle, in particular for urgent or emergency medical applications.

A subsequent whole blood separation into plasma/serum can be advantageous for point-of-care testing devices, which are used to provide a quick blood analysis at/near the patient to get a quick blood analysis result outside of a clinical laboratory to make immediate decisions about patient care. Typically point-of-care testing is performed by non-laboratory personnel. A quick foregoing plasma filtration process facilitates the quick blood analysis and enables new operating conditions for point-of-care devices, since most of them work with whole blood or with the aforementioned microdevices which lead to a very small yield of plasma/serum volume. The whole blood separation process can also be integrated within the point-of-care device.

SUMMARY OF THE INVENTION

The present invention provides a blood filtering device allowing a quick separation of blood components and an apparatus with reduced complexity in accordance with the subject-matter of the independent claim, wherein further embodiments are disclosed in the dependent claims.

According to the invention, a blood filtering device is provided including a housing, a filtration section, a first variable blood reservoir volume, and a receptacle configured to receive a second variable blood reservoir volume, wherein the filtration section comprises a raw side and a clean side separated by a filter medium, wherein the filtration section comprises a first communication path between the raw side and the first variable blood reservoir volume and comprises a second communication path between the raw side and the receptacle so that upon variation of one variable blood reservoir volume, blood in one of the first variable blood reservoir volume and a second variable blood reservoir volume coupled to the receptacle flows through the respective associated communication path to the raw side, wherein blood plasma/serum may pass through the filter medium and the residual blood flows through the other of the respective communication paths into the other one of the first variable blood reservoir volume and the second variable blood reservoir volume coupled to the receptacle.

Thus, a blood filtering device is provided for receiving, for example, an external blood reservoir as the second variable blood reservoir volume; this external blood reservoir may be used to take blood from a patient. This external blood reservoir may, for example, be a syringe, so that blood may be taken from the patient. After the patient's blood has been received in the external (second) blood reservoir, the external blood reservoir can be coupled to the receptacle of the blood filtering device so that the filtering process can be started immediately. Such a blood filtering device provides a modular component solution of low complexity enabling a simple, easy, quick separation of blood plasma/serum. The blood may be delivered by applying a pressure to the variable blood reservoir volume to be coupled so that the blood enters the filtration section by flowing through the communication path between the received variable blood reservoir volume and the filtration section. The filtration section separates the blood plasma/serum from the remaining cells of the blood so that the plasma/serum passes through the filter medium from the raw side to the clean side. The remaining blood cells and also possibly remaining plasma/serum, which has not yet passed through the filter medium, leave the filtration section through the communication path to the other (first) variable blood reservoir volume so that the remaining cells and the remaining plasma/serum collect in the other (first) variable blood reservoir volume fixedly connected to the blood filtering device. The other (first) variable blood reservoir may also be removable and may be designed as a syringe.

Afterwards, the blood can be forced again through the filtration section from the first variable blood reservoir volume, fixedly connected to the blood filtering device, through the filtration section to the second variable blood reservoir volume being connected to the blood filtering device. Thus, the process may be reversed and successively repeated so that by applying several iterations of cross-flow filtration, a considerable amount of plasma/serum may be collected in the filtration section, in particular at the clean side of the filtration section within a short time and by a device that is easy to handle. The collected plasma/serum may be used for further analysis.

According to an exemplary embodiment, the first variable blood reservoir volume is defined by a tubular volume and a movable piston arranged therein.

Thus, it is possible to provide a variable blood reservoir volume which can be filled and emptied by applying a force to the movable piston so as to force the blood out of the tubular volume of the first variable blood reservoir volume through the filtration section into the variable blood reservoir volume coupled to the blood filtering device.

According to an exemplary embodiment, the movable piston is coupled to a rod extending along and through the tubular volume.

Thus, the user can apply a force onto the movable piston, even when the variable blood reservoir volume is disposed inside a housing. In other words, by applying a force onto the rod, the piston can be moved forward to apply a pressure to the first variable blood volume to force the blood through the filtration section.

According to an exemplary embodiment, a piston of the first variable blood reservoir volume and a piston of a second variable blood reservoir volume to be coupled to the receptacle have opposite push directions.

Thus, a blood filtering device that has an external (second) variable blood reservoir volume coupled thereto that is also provided with a piston and possibly a rod so that a user may apply successively a force onto the rod of the external variable blood reservoir volume and onto the rod of the internal variable blood reservoir volume. In particular, it is possible to hold the blood filtering device in one hand and apply a pressure onto one of the rods by means of the thumb, successively release the first rod and push the entire blood filtering device with the push button of the other rod onto an abutment to apply a force onto the other rod. Thus, a blood flow through the filtration section in successively opposite directions can be generated quickly and easily.

According to an exemplary embodiment, the blood filtering device further comprises a resilient element functionally coupled between the movable piston and the housing so as to provide a force to move the piston in a direction toward the first communication path.

Thus, it is possible to store energy when forcing the blood through the filtration device into the first variable blood reservoir volume; when releasing the rod or piston of the coupled variable blood reservoir volume, the resilient element may apply the counterforce to generate a flow back into the blood reservoir volume which is coupled to the blood filtering device.

According to an exemplary embodiment, the rod of the first variable blood reservoir on a distal end opposite the piston comprises a push button, wherein the resilient element is a coil spring between the push button and the housing.

Thus, it is possible to easily apply a force by the thumb, for example, onto the rod by pushing the push button, wherein the push button at the same time serves as an abutment for the resilient element or as a fixation of the resilient element, depending on the kind of resilient element. For example, the resilient element may be provided at the push button of the first variable reservoir.

According to an exemplary embodiment, the receptacle is configured to receive a syringe as the second variable blood reservoir volume.

Thus, it is possible to employ a standard device that is available almost always and everywhere as the second variable blood reservoir volume. It should be noted that a monovette may be used instead of a syringe. The blood filtering device may have a needle or cannula adapted to perforate a septum of the monovette.

According to an exemplary embodiment, the receptacle has a bay with a longitudinal extension for receiving a syringe housing, wherein the longitudinal extension of the bay is parallel to the longitudinal extension of the tubular volume.

Thus, it is possible to arrange the external second variable blood reservoir volume, e.g. a syringe, and the first variable blood reservoir volume in a space-saving manner, thereby providing a compact blood filtering device, even when the second variable blood reservoir volume is coupled to the blood filtering device. The receptacle and the bay may be designed as a Luer/Luer lock connection with a clip-mounting mechanism for the syringe or monovette.

According to an exemplary embodiment, the bay and the tubular volume of the first variable blood reservoir volume are arranged side by side.

Thus, it is possible to provide a blood filtering device of a compact design.

According to an exemplary embodiment, the blood filtering device further comprises a plasma/serum outlet in the housing, wherein the plasma/serum outlet is connected to the clean side of the filtration section.

Thus, it is possible to extract the gained plasma/serum from the blood filtering device, for example, in order to supply the gained plasma/serum to an analysis procedure.

According to an exemplary embodiment, the plasma/serum outlet is covered by a pierceable septum.

Thus, it is possible to pierce the septum, for example, by a needle of a further syringe to extract the plasma/serum from the clean side volume of the filtration section.

According to an exemplary embodiment, the filter medium comprises a hollow fiber or a hollow fiber bundle.

Thus, it is possible to conduct a reliable and effective filtering process. It should be noted that, instead of hollow fibres, a flat filter medium or membrane may be used also.

It should be noted that the above features may also be combined. The combination of the above features may also lead to synergetic effects, even if not explicitly described in detail. These and other aspects of the invention will be become apparent from and be elucidated with reference to the embodiments described hereinafter.

BRIEF DESCRIPTION OF THE DRAWINGS

Exemplary embodiments of the present invention will be described in the following with reference to the following drawings.

FIG. 1 illustrates a schematic overview of a blood filtering device according to an exemplary embodiment.

FIG. 2 illustrates a schematic overview of a filtration section of the blood filtering device according to an exemplary embodiment.

FIG. 3 illustrates a perspective view of a blood filtering device and a variable blood reservoir volume to be coupled in a half-cut view.

FIG. 4 illustrates the coupling process/insertion of the external variable blood reservoir volume into the blood filtering device according to an exemplary embodiment.

FIG. 5 illustrates the use of the blood filtering device according to an exemplary embodiment.

DESCRIPTION OF THE INVENTION

Figure 6:
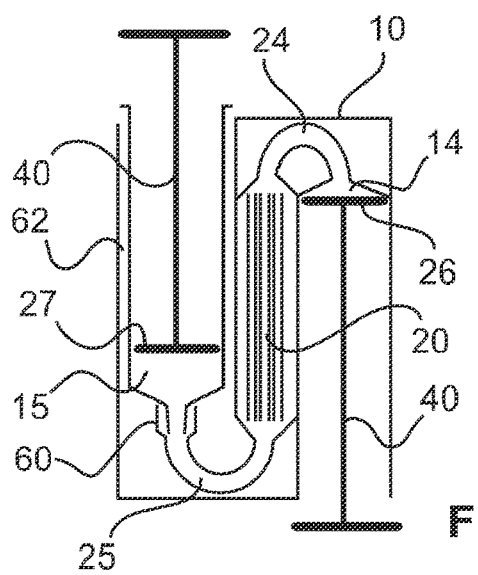
FIG. 6 illustrates a schematic overview of an exemplary embodiment of the blood filtering device.

FIG. 1 illustrates an exemplary embodiment of a blood filtering device. The blood filtering device 1 comprises a housing 10 and a filtration section 20. The blood filtering device 1 further comprises a first variable blood reservoir volume 14 and a receptacle 60 for a further second variable blood reservoir volume 15 to be coupled to the receptacle 60. The filtration section 20, here arranged between the two variable blood reservoir volumes, comprises a raw side 21 and a clean side 22 separated by a filter medium 23. Thus, blood on the raw side 21 may pass through the filter medium to be filtered so that the result of the filtration process, i.e. the plasma/serum, arrives at the clean side 22 of the filtration section 20. The filtration section 20 comprises a first communication path 24 between the raw side 21 and the first variable blood reservoir volume 14 and a second communication path 25 between the raw side 21 and the receptacle 60 so that, upon variation of one of the two variable blood reservoir volumes 14, 15, blood in one of the first variable blood reservoir volume 14 and the external second variable blood reservoir volume 15, now being coupled to the receptacle 60, flows through the respective communication path 24, 25 to the raw side 21, wherein the blood plasma/serum may pass through the filter medium 23. The residual blood flows through the other of the respective communication paths 24, 25 into the other of the first variable blood reservoir volume 14 and the external second variable blood reservoir volume 15 that is coupled to the receptacle 60 as shown in FIG. 1.

It should be noted that the details of the filtration section 20 can be seen in FIG. 2. FIG. 2 illustrates the filtration section including the raw side 21, the clean side 22, and the filter medium 23 separating the raw side 21 and the clean side 22. It should be noted that the filtration section 20 may be separated from the blood filtering device, in particular in case of a terminated filtration process. The filtration section 20 in FIG. 2 has a plasma/serum outlet 16, which in FIG. 2 is closed by a septum 18. It should be noted that the septum may be pierceable. It should also be noted that the septum may be transmissive for gas so that a built-up pressure may escape or a built-up vacuum may be balanced through the septum 18.

FIG. 3 illustrates a perspective half-cut view of a blood filtering device according to an exemplary embodiment, wherein the external variable blood reservoir volume 15 is separated from the blood filtering device 1. The second, external variable blood reservoir volume 15 may be used for taking blood from a patient by coupling a needle (not illustrated) to an opening and by pulling the rod 40 to draw the blood into the variable volume 15. For this purpose, the proximal first end 41 of the rod 40 may be coupled to a plunger 27. A push button 43 may be coupled to the distal second end 42 of the rod 40. Thus, the rod 40 may be pushed and pulled forward and backward by gripping the push button 43 so as to move the piston 27 to enlarge or reduce the variable blood reservoir volume 15. When the second variable blood reservoir volume 15 is loaded with blood, the second variable blood reservoir volume 15 may be coupled to the receptacle 60 of the blood filtering device 1. Now, the push button 43 may be pushed so as to force the blood contained in the second variable blood reservoir volume 15 through the communication path 25 into the filtration section 20 so that the filtration process can take place. Plasma/serum can pass through the filter medium (not illustrated) and the remaining blood and the remaining plasma/serum may exit the filtration section 20 through the communication path 24 and flow into the first variable blood reservoir volume 14. The piston 26 of the first variable blood reservoir volume 14 is pushed outward when increasing the volume 14, so that the rod 40 of the second volume 14 moves outward. When the second variable blood reservoir volume 15 is empty, the maximum amount of blood has reached the first variable blood reservoir volume 14 so that the process may be reversed by pushing the other push button 43 to force the blood from the first variable blood reservoir volume 14 through the communication path 24 into the filtration section 20 and then further through the communication path 25 into the second variable blood reservoir volume 15. This process may be repeated several times so that a cumulative amount of plasma/serum may be collected in the filtration section 20, i.e. the clean side 22 of the filtration section 20, which has been described and illustrated in FIG. 2.

FIG. 4 illustrates the process of coupling the second variable blood reservoir volume 15 to the blood filtering device 1. For this propose, the user may hold the housing 10 with his hand 80 and insert the second variable blood reservoir volume 15 into the bay 62 to couple the second variable blood reservoir volume 15 to the receptacle 60. After having coupled the external second variable blood reservoir volume 15, for example, in form of a syringe, to the receptacle 60, the filtration process can be started by pushing the push button 43, as can be seen in FIG. 5. When having pushed down entirely the push button 43 of one of the first or second variable blood reservoir volumes, the push button 43 may be released, and the other push button 43 may be pushed. Pushing the other push button may be achieved by pressing the other push button onto an abutment, for example, a desk or any other surface 90. When having arrived at the end position, the first push button 43 may be pressed again by the thumb of the user or may be pressed against surface 90.

It should be noted that the filtration device may also be operated by any other finger or any other body part. For example, the first push button may be also pushed by an external abutment or surface. Thus, the device may be operated with one hand.

It should be noted that the filter housing and the device may be produced of material which may be sterilized. The filter medium may be a hollow fiber membrane or a bundle of hollow fibers. However, a flat sheet membrane may also be used as a filter medium. Typically, the filtration operation is done by a cross-flow mode. It should be noted that the filtration section 20 may be designed as an exchangeable part so as to combine different filtering types, for example, for obtaining different portions of the blood. It should be noted that several portions of the filtration device may be coated with heparin so that the blood condition may be kept sufficient for a filtration process. It should be noted that the blood filtering device may have couplings or other elements to eliminate an overpressure or too strong a force being applied to the respective variable filter volume. It should be noted that instead of manual operation, also an electric or mechanic operation may be carried out, for example, when using the filtering device in connection with an automated drive. It should also be noted that the filtration section or one of the variable blood reservoir volumes or the communication paths may be used as a reservoir for additives to improve the filtration process.

FIGS. 6 to 10 illustrate several embodiments of a filtration device to be described in the following.

FIG. 6 illustrates an exemplary embodiment where the external second variable blood reservoir volume 15 is coupled to the blood filtering device through receptacle 60.

Figure 7:
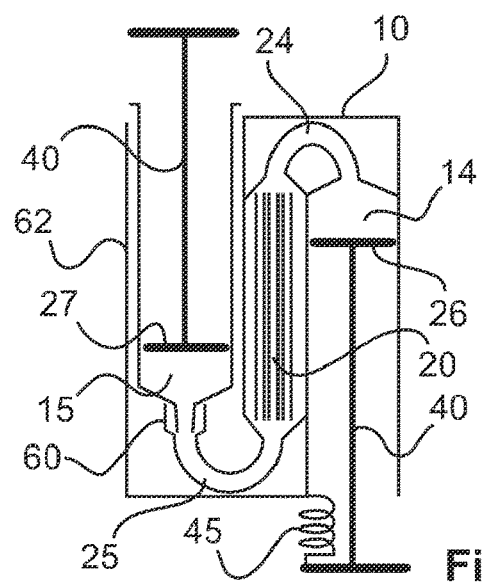
FIG. 7 illustrates an exemplary embodiment of a blood filtering device including a resilient element.

FIG. 7 illustrates an exemplary embodiment similar to that of FIG. 6 but provided with a resilient element 45. The resilient element 45 may be used to apply a force to the rod 40 of the first variable blood reservoir volume 14. When applying a force to the second external variable blood reservoir volume 15, the blood is forced through the communication path 25, the filtration section 20, and the first communication path 24 into the first variable blood reservoir volume 14 so that the resilient element is biased. When releasing the force applied onto the push button 43, i.e. onto the second variable blood reservoir volume 15, the resilient element 45 may push back the blood in a reverse flow direction. It should be noted that the resilient element 45 may be a spring biased in a pulling direction or a spring biased in a pushing direction.

Figure 8:
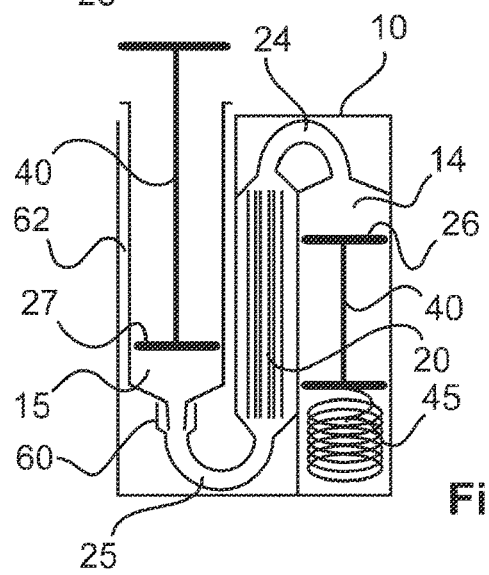
FIG. 8 illustrates an exemplary embodiment of the blood filtering device including an internal resilient element in form of a spring.

FIG. 8 illustrates a further exemplary embodiment similar to that of FIG. 7. The resilient element 45 is a spring which may be, for example, a push-biased spring, included in the housing 10. Thus, filling of the first variable blood reservoir volume 14 may bias the spring 45 so that a return flow will start when releasing the force applied on the plunger 27.

Figure 9:
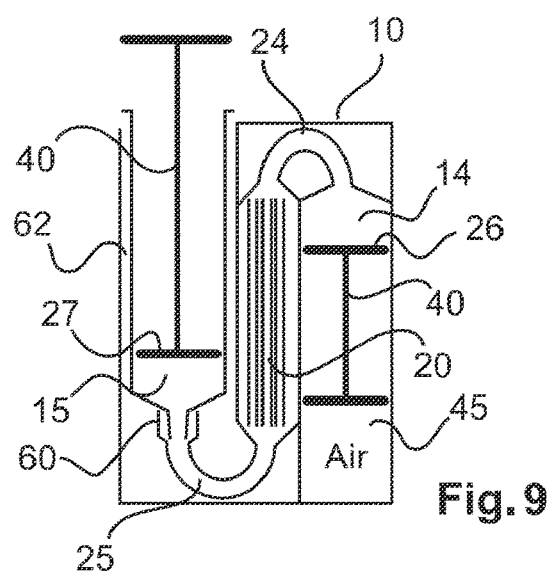
FIG. 9 illustrates an exemplary embodiment of the blood filtering device including an internal resilient element in form of a compressible air volume.

FIG. 9 illustrates a further exemplary embodiment, wherein the resilient element 45 is realized in the form of an air volume. The air in the air volume acting as resilient element 45 will be compressed and thus biased so that the rod 40 coupled to the plunger 26 will force the blood from the first variable blood reservoir volume 14 through the first communication path 24, the filtration section 20, and the second communication path 25 into the second variable blood reservoir volume 15 when releasing the force applied on the plunger 27.

The exemplary embodiment of FIG. 6 may be operated by holding the entire filtering device in one hand and by pushing the rod on the plunger 27 with a thumb or a finger and by applying the counterforce on the plunger 26 by applying a force in that the rod 40 coupled to the plunger 26 is pushed against an abutment. The exemplary embodiments of FIG. 7, FIG. 8, and FIG. 9 do not mandatorily require the application of an external counterforce to generate the return flow as the flow in the first direction will bias the resilient element 45 so that the force for return flow is applied by releasing the resilient element 45.

Figure 10:
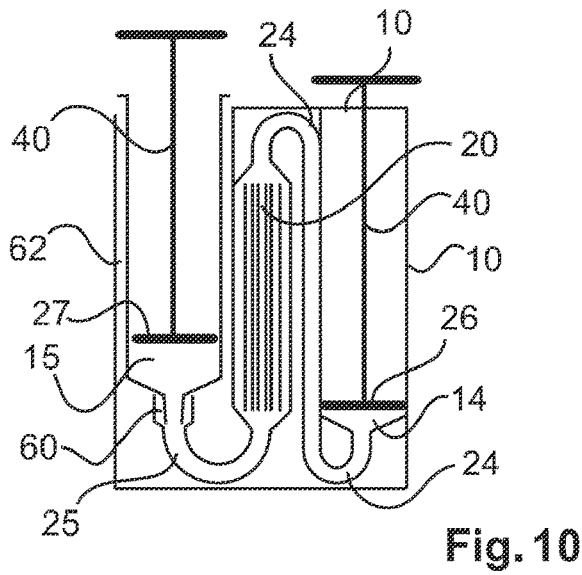
FIG. 10 illustrates an exemplary embodiment of the blood filtering device including parallel variable blood reservoir volumes with corresponding moving directions of the respective pistons.

FIG. 10 illustrates a further exemplary embodiment, wherein both variable blood reservoir volumes 14, 15 are arranged side by side and the pushing directions of the corresponding rods 40 correspond to each other. Thus, the device may be handheld and the user may apply a force onto one rod until reaching the end position and then change the thumb or the finger and apply pressure to the other rod until reaching the end position; this procedure is repeated until a sufficient amount of serum/plasma has been gained in the filtration section 20.

It should be noted that the blood filtering device as described above allows a fast and simple separation process to separate blood into the cells and the liquid phase of blood. The device allows a one-handed operation; some of the embodiments require a manual actuation of only one plunger. In particular, a manual operation is possible without electrical support action, however, it should be noted that an electrical drive may be used also. The simple and compact construction of the blood filtering device allows shaking by hand of the filter housing for effecting a mixing of the blood sample to keep the suspension well-mixed and to avoid settling of the solid components. Further, when pre-treatment components are included, a stabilizing process may be obtained, for example, when mixing the whole blood with heparin. The closed and sealed filtering device can be disposed completely at the end, when the critical materials are treated. No opening of the device is required. When employing a transparent material, a direct observation of the filtration process is possible. It should be noted that a syringe for blood withdrawal can directly be inserted in the bay 62 with receptacle 60 and be used for filtration so that no decanting of blood from a syringe for blood withdrawal to another container is necessary.

While specific embodiments of the invention have been shown and described in detail to illustrate the inventive principles, it will be understood that the invention may be embodied otherwise without departing from such principles.

What is claimed is:

1. A blood filtering device comprising:
a housing;
a filtration section disposed in the housing;
a first tubular variable volume blood reservoir arranged in the housing and having:
   a first piston movably arranged within the first tubular variable volume blood reservoir, the first piston movable to vary a first blood reservoir volume of the first tubular variable volume blood reservoir;
a second tubular variable volume blood reservoir having:
   a second piston movably arranged within the second tubular variable volume blood reservoir, the second piston movable to vary a second blood reservoir volume of the second tubular variable volume blood reservoir;
a receptacle disposed in the housing and configured to receive and fluidically connect to the second blood reservoir volume of the second tubular variable volume blood reservoir;
a rod arranged in an interior of the first tubular variable volume blood reservoir, the rod movable relative to the housing and the first tubular variable volume blood reservoir, the rod extending along and through the first blood reservoir volume, the rod comprising:
   a first end having the first piston coupled thereon, the first piston contacting against blood in the first tubular variable volume blood reservoir; and
   a second end of the rod having a push button;
a coil spring having:
   a first end pressing against the housing in which the filtration section and the first tubular variable volume blood reservoir are both arranged; and
   an opposite second end pressing against the push button of the rod, wherein the coil spring acts against the housing, urging the first piston to move relative to the first tubular variable volume blood reservoir and the housing, to apply pressure to blood in the first blood reservoir volume, urging the blood to flow into the filtration section;
wherein the filtration section comprises
   a filter medium separating a raw side and a clean side from each other;
wherein the filtration section comprises
   a first communication path fluidically connecting the raw side and the first variable blood reservoir volume to each other and further comprises
   a second communication path fluidically connecting the raw side and the receptacle to each other;
wherein, upon variation of the first variable blood reservoir volume by the coil spring apply pressure to blood in the first blood reservoir volume, blood contained in the first variable blood reservoir volume flows through the first communication path to the raw side and blood plasma/serum of the blood passes through the filter medium from the raw side to the clean side while residual blood flows from the raw side through the second communication path into the second variable blood reservoir volume coupled to the receptacle, and, upon variation of the second variable blood reservoir volume coupled to the receptacle by actuation of the second piston apply pressure to blood in the second blood reservoir volume, blood contained in the second variable blood reservoir volume flows through the second communication path to the raw side and blood plasma/serum of the blood passes through the filter medium from the raw side to the clean side while residual blood flows from the raw side through the first communication path into the first variable blood reservoir volume, compressing the coil spring.

2. The blood filtering device according to claim 1, wherein
the first tubular variable blood reservoir volume is an internal variable blood reservoir volume disposed in the housing.

3. The blood filtering device according to claim 1, wherein
the first tubular variable blood reservoir volume is fixedly connected to the blood filtering device.

4. The blood filtering device according to claim 1, wherein
the first piston and the second piston have oppositely oriented push directions.

5. The blood filtering device according to claim 1, wherein
the second tubular variable volume blood reservoir is a syringe; and
the receptacle is configured to receive the syringe.

6. The blood filtering device according to claim 5, wherein
the receptacle comprises
a bay comprising a longitudinal extension configured to receive a syringe housing of the syringe,
wherein the longitudinal extension of the bay extends parallel to a longitudinal extension of the first tubular variable volume blood reservoir.

7. The blood filtering device according to claim 6, wherein
the bay and the first tubular variable volume blood reservoir are arranged side by side.

8. The blood filtering device according to claim 1, wherein
the filtration section comprises
a plasma/serum outlet and
the plasma/serum outlet is connected to the clean side of the filtration section.

9. The blood filtering device according to claim 8, further comprising
a pierceable septum that covers the plasma/serum outlet.

10. The blood filtering device according to claim 1, wherein
the filter medium comprises a hollow fiber or a hollow fiber bundle.

* * * * *